United States Patent [19]

Müller et al.

[11] Patent Number: 5,066,292
[45] Date of Patent: Nov. 19, 1991

[54] CATHETER SYSTEM FOR VESSEL RECANALIZATION IN THE HUMAN BODY

[75] Inventors: Gerhard Müller; Hasan Kar; Klaus Dörschel, all of Berlin; Karl-Heinz Schönborn, Mainz, all of Fed. Rep. of Germany

[73] Assignee: Schott Glaswerke, Mainz, Fed. Rep. of Germany

[21] Appl. No.: 494,743

[22] Filed: Mar. 19, 1990

[30] Foreign Application Priority Data

Mar. 17, 1989 [DE] Fed. Rep. of Germany ... 8903333[U]

[51] Int. Cl.$^5$ ............................................. A61M 29/02
[52] U.S. Cl. ......................................... 606/7; 606/15; 606/16; 128/398
[58] Field of Search ......................... 606/2, 7, 10–17; 604/19, 21; 128/634, 6, 395–398; 219/121.6–121.62

[56] References Cited

U.S. PATENT DOCUMENTS

| | | | |
|---|---|---|---|
| 4,669,467 | 6/1987 | Willett et al. | 606/7 |
| 4,790,310 | 12/1988 | Ginsburg et al. | 606/7 |
| 4,800,876 | 1/1989 | Fox et al. | 606/7 |
| 4,848,336 | 6/1989 | Fox et al. | 606/7 |

Primary Examiner—Stephen C. Pellegrino
Assistant Examiner—Steven J. Shumaker
Attorney, Agent, or Firm—Millen, White & Zelano

[57] ABSTRACT

A catheter for vascular surgery includes a circular array of lightguides disposed at the distal end of the catheter about an inflatable balloon. Upon pressurizing the balloon the diameter of the catheter expands. The lightguides are bunched at the end of the catheter proximate the source of laser light where shutters are positioned for selecting only those lightguides at the distal end which are needed to remove blockages.

4 Claims, 1 Drawing Sheet

CATHETER SYSTEM FOR VESSEL RECANALIZATION IN THE HUMAN BODY

BACKGROUND OF THE INVENTION

The invention relates to a catheter system for the transmission of laser radiation for treatment purposes, especially in vascular systems of the human body. It is known that certain deposits in vascular systems, for example of the human body, especially in blood vessels, can be detached by laser radiation of a certain energy density, presumably as a consequence of the photohydraulic effect, and the thus-treated vessels can therefore be recanalized. A catheter system for such applications has been disclosed, for example, in DOS 3,739,965.

Preferably, such catheter systems utilize an annular catheter with an inner duct around which inner duct the wall structure of the catheter retains a circular array of optical fibers for transmitting the laser light to the treatment site at the distal end of the catheter.

It is important in the design of such an annular catheter to ensure that the laser light exiting from the ring-shaped array of optical fibers impinges upon the deposits in the peripheral zone of the vessel which is to be canalized by the laser radiation. Therefore, the diameter of the ring-shaped lightguide arrangement has been chosen, in general, so that the lightguides are located along a peripheral circle corresponding approximately to the deposits. Such a catheter is then introduced into the vessel to be treated up to the point of constriction and can be advanced further only to the extent to which the deposits on the outer wall of the vessel have been removed by the treatment. In order to place the catheter in the right direction with progressing treatment and additional attempts at advancement, the inner duct provided in the catheter, or the lumen, is utilized. Besides being used as a flow channel for rinsing fluid, it can also for the insertion of a thinner guide wire which can be pushed forward even through the as yet untreated constriction sites. It then serves as a guide route for the further advancement of the annular catheter during the course of the treatment.

However, it is not always possible and therefore desirable to employ annular catheters with a diameter already corresponding extensively to the internal diameter of the vessel to be recanalized. It is desirable, especially for guiding a laser catheter forward into regions of a smaller vessel diameter, for example in the lower leg level of a patient or into cardiac coronaries, to utilize lightguide catheters having maximally small diameter which, if at all possible, is to range even below 5 French.

It can be derived, for example, from DOS 3,739,965 that, depending on the optical emergence characteristic of the distal end of the lightguide catheter, the energy density of the laser radiation decreases already with a small distance from the emergence surface to such an extent that it is no longer sufficient for an effective removal of plaques in vessels. This can occur, in particular, when a relatively thin annular catheter is employed; when the deposits to be removed are located asymmetrically on one side, for example in a flaring portion of the vessel; or when such deposits are outside of the diametrical range of the catheter. In such cases, it may become unavoidable to replace the catheter utilized, as required, by a catheter having a larger or smaller internal diameter adapted to the respective lumen of the vessel.

SUMMARY OF THE INVENTION

The invention is based on the object of further developing a catheter system of the type discussed hereinabove in such a way that the diameter of the annular lightguide catheter can be kept at a minimum, but the laser radiation, if needed, can be directed so that it is capable of effectively removing deposits which lie substantially outside of the diameter of the annular catheter.

Elastically expansible connecting members preferably of polymethylsiloxane, between the optical fibers of the lightguide ring make it possible for the lightguides not only to occupy an annular emergence area of a larger diameter, due to a parallel-displacing widening of the ring, but also make it possible to widen the ring of lightguides in a divergent fashion. This latter feature is achieved by means of a gradually increasing elasticity of the connecting material between the optical fibers toward the distal end of the catheter, or, respectively, by limiting the elastic design to only a small longitudinal section before the emergence end of the catheter. Accordingly, the laser radiation emerging from the lightguides is oriented in each case away from the axis of the catheter toward the vessel wall.

Since a single lightguide, however, generally does not carry enough laser energy in order to effect detachment of vessel deposits, a uniform expansion of the ring of lightguides at the distal end of the catheter can lead to an undesirable reduction in the energy density of the radiation due to the increase in the mutual spacing of the individual lightguides. In a preferred embodiment of the invention, the optical fibers are, therefore, firmly jointed in groups at the distal end over the periphery of the annular catheter, the elastic expandibility being limited solely to transition zones between these groups. Consequently, the effect is achieved of a group of several optical fibers which essentially maintain their mutual spacings can be deflected toward the vessel wall. In such a case, based on this group of lightguides, the required energy density remains preserved.

Since the vessel deposits frequently occur in an asymmetrical fashion and consequently only specific regions of the inner vessel wall are to be treated in many cases, it is anyway not always required generally to feed laser light to the entire ring of lightguides. For this purpose the invention furthermore provides that the lightguide fibers are combined, at the proximal inlet end of the annular catheter, into specific groups to which laser light can be supplied selectively. These groups are, of course, preferably identical to the groups of fixedly joined optical fibers at the distal end of the catheter. In order to incur minimum input radiation losses and to avoid destruction of the amount of optical fibers at the proximal end due to laser radiation not coupled into the optical fibers, the fibers at the proximal end of the catheter are preferably arranged in a hexagonally densest packing, these groups of optical fibers forming coherent regional areas of the hexagonal packing. These regional areas can be, for example, parallel area strips of the hexagonal packing. Such strips can be faded out in a simple way by means of parallel sliding stops or the like.

Widening of the ring of optical fibers are the distal end of the catheter can be brought about, for example, by a chamber which can be supplied with a pressure fluid. It is also possible to provide component chambers distributed over the periphery of the catheter, with the aid of which an expansion of the annular catheter can be effected only in specific peripheral zones wherein then additionally the lightguide fibers can be selectively exposed to laser light.

Inasmuch as the catheters in question are however generally already equipped with an inner duct for other reasons, as mentioned above, the invention provides in a preferred embodiment to include a miniature dilation catheter which can be introduced up to the distal end into the inner duct of the annular catheter and can be expanded at that distal end in order to expand the ring of lightguides in its entirety or in a controlled, radial direction.

There are various possibilities of determining and observing the treatment of only a specific inner wall region by selective activation of optical fibers. Thus, individual ones of the optical fibers of the ring can be utilized for illumination of the treatment site, which latter can then be observed by way of an endoscope inserted in the inner duct of the catheter. It is also possible to recognize, by analysis of radiation reflected from the treatment site, whether there are indeed deposits or tissues of the vessel wall in the intended irradiation zone. Such methods are, however, known in part and are not the subject of this invention. Even if the expansibility of the ring of lightguides at the distal end of the catheter is restricted to only a certain peripheral range, this range can generally be placed into the desired treatment position by exerting a rotary force on the catheter, if necessary, with a certain axial to and for movement at the proximal end.

Owing to the design of the catheter system in accordance with this invention, it is possible, even with the use of a very thin laser ring catheter, to treat regions of a vessel wall by laser irradiation which lie at a distance from the axis of the catheter that can be larger than the radius of the annular catheter. The arrangement of this invention is of advantage even in the case of deposits lying within the peripheral zone of the catheter end since, due to the divergent deflecting ability of the ends of the optical fibers, a higher energy density can be achieved for the detachment of the deposits because in certain cases the procedure can be performed with a steeper angle of incidence of the laser beam onto the site to be treated.

Even on those occasions where laser catheters must be guided forward into regions of smaller vessel diameters, this can be easily realized by means of the arrangement of this invention due to the elastic connections between the optical fibers or fiber groups. In this context, the distal end can be made to approach the vessel deposits without any problems, especially after a repeated, gentle reciprocating motion of the catheter. A change of catheters, as required in most instances in such cases according to the state of the art thus far, is eliminated.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire disclosures of all applications, patents and publications, if any, cited above and below, and of corresponding application Federal Republic of Germany G 89 03 333.7 filed Mar, 17, 1989, are hereby incorporated by reference.

DETAILED DESCRIPTION OF THE DRAWINGS

Figure 1:
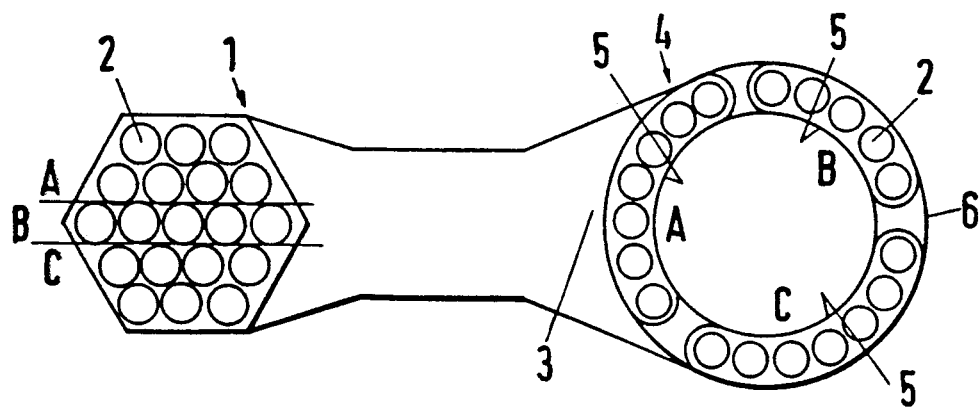
FIG. 1 shows a schematic view of the association of the fiber groups at the distal end with respect to the fiber groups in a hexagonally densest packing at the proximal end of the catheter.

FIG. 1 illustrates the proximal and distal ends in a schematic view. The proximal end 1 consists of the hexagonally densest packing of the individual optical fibers 2. In the lightguide ring 3 at the distal end 4, the optical fibers 2 are in each case fixedly joined into peripheral groups 5, and the individual groups A, B, C are connected, in turn, by way of elastically deformable intermediate zones 6. The respective peripheral groups 5 at the distal end, consisting of firmly joined optical fibers 2, correspond at the proximal end to the respective parallel regional areas A, B, C of the hexagonal packing.

Figure 2:
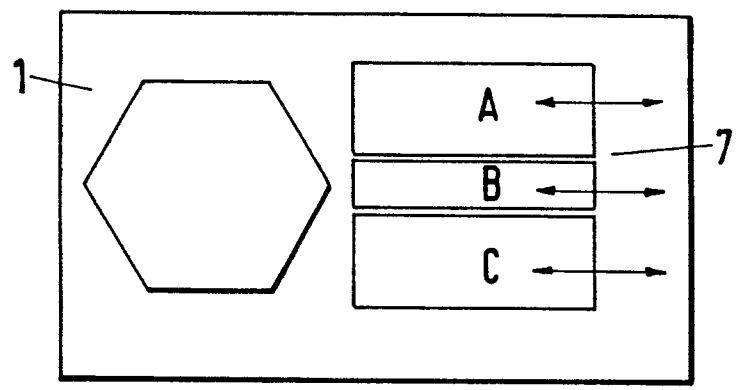
FIG. 2 shows a schematic illustration of the sliding stops for fading out the corresponding area strips on the hexagonally densest fiber packing at the proximal end of the catheter.

These regional areas A, B, C can be faded out, by means of the sliding stops 7 represented in FIG. 2, individually or respectively in twos at the same time, so that respectively only one or two fiber groups A, B, C can be exposed to laser light at the distal end.

Figure 3:
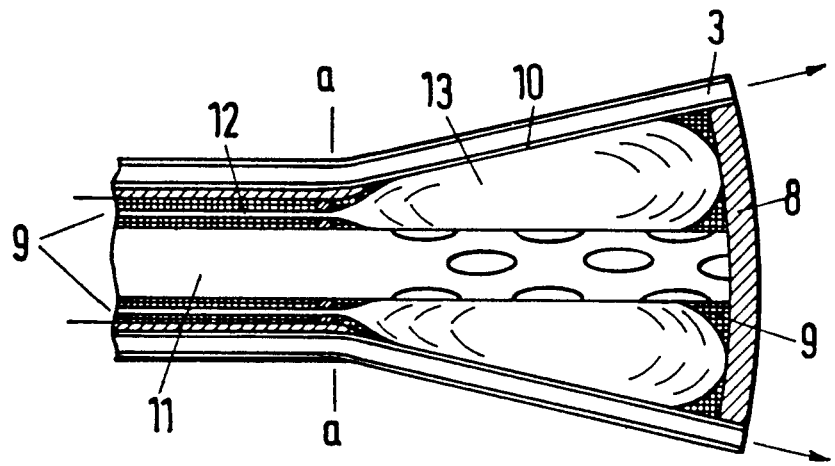
FIG. 3 is a longitudinal section through the distal end of the ring catheter with the miniature dilation catheter having been introduced, and with expanded lightguide ring.

FIG. 3 shows that a miniature balloon dilating catheter 9 is introduced into the inner duct 8. Feeding channels 12 for a pressure fluid are provided between the casing 10 of this miniature catheter and its inner duct 11; these feeding channels terminate at point a in each case into a balloon 13. Under exposure to pressure, the balloons, preferably at least three, expand the lightguide ring 3 at the distal end over the longitudinal section starting with point a up to the end of the catheter on the light emergence side, with deformation of the elastic intermediate zones 6.

In another preferred embodiment, not illustrated herein, the feed channels for pressure fluid and the distending means in the distal end zone can be integrated directly in the fiber ring of the catheter whereby the distensible pressure chambers come to lie directly in the elastic connecting sections 6 in the distal end zone. Consequently, with pressure being exerted on respectively two neighboring pressure chambers, the interposed zone with firmly joined optical fibers can then be selectively bent away in toward the vessel wall.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A catheter system for the transmission of laser radiation comprising:
   a catheter having a proximate end for coupling to a source of laser light and a distal end for emitting the laser light, the catheter having a wall with an inner surface defining a cavity;
   a ring of lightguides extending through the cavity adjacent the inner surface of the catheter wall, the ring of lightguides being configured in separate connected groups with the groups connected by elastically extendable material; and
   means adjacent the distal end and disposed within the ring of lightguides for selectively outwardly expanding and contracting the diameter of the entire ring of lightguides or selectively the individual groups of lightguides, the lightguides being bunched at the proximate end of the catheter for alignment with the source of laser light.

2. The catheter system of claim 1, further including shutter means adjacent the proximate end between the proximate end and source of laser light for selecting those lightguides which are to be illuminated with laser radiation.

3. The catheter system of claim 2, wherein the lightguides are bunched into a hexagonal array at the proximate end.

4. The catheter of claim 1, wherein the lightguides are grouped in arcuate, rigid arrays at the distal end of the catheter, each array being connected to adjacent arrays by said elastically extendable material.

* * * * *